US011078241B2

(12) United States Patent
Upmeier et al.

(10) Patent No.: US 11,078,241 B2
(45) Date of Patent: Aug. 3, 2021

(54) MULTI-EPITOPE FUSION PROTEIN OF AN HCV ANTIGEN AND USES THEREOF

(71) Applicant: Roche Diagnostics Operations, Inc., Indianapolis, IN (US)

(72) Inventors: Barbara Upmeier, Iffeldorf (DE); Ralf Bollhagen, Penzberg (DE); Toralf Zarnt, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 16/751,609

(22) Filed: Jan. 24, 2020

(65) Prior Publication Data
US 2020/0148726 A1 May 14, 2020

Related U.S. Application Data

(63) Continuation of application No. PCT/EP2018/069985, filed on Jul. 24, 2018.

(30) Foreign Application Priority Data

Jul. 27, 2017 (EP) .................................... 17183523

(51) Int. Cl.
*C07K 14/005* (2006.01)
*G01N 33/576* (2006.01)
(52) U.S. Cl.
CPC ....... *C07K 14/005* (2013.01); *G01N 33/5767* (2013.01); *C07K 2319/35* (2013.01); *C12N 2770/24222* (2013.01); *G01N 2333/186* (2013.01); *G01N 2469/10* (2013.01)
(58) Field of Classification Search
None
See application file for complete search history.

(56) References Cited

U.S. PATENT DOCUMENTS

2009/0186045 A1* 7/2009 Ray ........................ A61K 39/12
424/189.1
2009/0291892 A1 11/2009 Scholz et al.

FOREIGN PATENT DOCUMENTS

| DE | 3640412 A1 | 6/1988 |
|---|---|---|
| EP | 1308507 A2 | 5/2003 |
| EP | 0967484 B1 | 5/2007 |
| WO | 2000/031127 A2 | 6/2000 |
| WO | 2003/000878 A2 | 1/2003 |
| WO | 2009/056535 A2 | 5/2009 |
| WO | 2013/107633 A1 | 7/2013 |
| WO | 2016/069762 A2 | 5/2016 |
| WO | 2016/091755 A1 | 6/2016 |
| WO | 2016/172121 A1 | 10/2016 |

OTHER PUBLICATIONS

Ferroni et al. Identification of Four Epitopes in Hepatitis C Virus Core Protein. J. Clin. Microb., 1993, 31: 1586-1591.*
Cpaperone (protein)—Wikipedia. Downloaded Nov. 17, 2020/.*
Boulant, Steeve et al., Hepatitis C Virus Core Protein Is a Dimeric Alpha-Helical Protein Exhibiting Membrane Protein Features, Journal of Virology, 2005, pp. 11353-11365, vol. 79, No. 17.
Chen, Yiyan and Baker, Gregory L., Synthesis and Properties of ABA Amphiphiles, The Journal of Organic Chemistry, 1999, pp. 6870-6873, vol. 64.
Chien, David Y. et al., Use of a Novel Hepatitis C Virus (HCV) Major-Epitope Chimeric Polypeptide for Diagnosis of HCV Infection, Journal of Clinical Microbiology, 1999, pp. 1393-1397, vol. 37, No. 5.
Galdino, Alexsandro S. et al., A Novel Structurally Stable Multiepitope Protein for Detection of HCV, Hepatitis Research and Treatment, 2016, 9 pp., vol. 2016, Article ID 6592143.
International Search Report dated Sep. 25, 2018, in Application No. PCT/EP2018/069985, 4 pp.
Messina, Jane P. et al., Global Distribution and Prevalence of Hepatitis C Virus Genotypes, Hepatology, 2015, pp. 77-87, vol. 61.
Sabet, Leila Pishraft et al., Immunogenicity of Multi-Epitope DNA and Peptide Vaccine Candidates Based on Core, E2, NS3 and NS5B HCV Epitopes in BALB/c Mice, Hepatitis Monthly, 2014, 9 pp., vol. 14, No. 10, e22215.
Seitz, Oliver and Kunz, Horst, HYCRON, an Allylic Anchor for High-Efficiency Solid Phase Synthesis of Protected Peptides and Glycopeptides, The Journal of Organic Chemistry, 1997, pp. 813-826, vol. 62.
Tanaka, Yasuhito et al., High stability of enzyme immunoassay for hepatitis C virus core antigen-evaluation before and after incubation at room temperature, Hepatology Research, 2003, pp. 261-267, vol. 26.

* cited by examiner

*Primary Examiner* — Nianxiang Zou
(74) *Attorney, Agent, or Firm* — Stinson LLP (57) ABSTRACT

The disclosure relates to a multi-epitope fusion protein as well as to its use as calibrator and/or control in an in vitro diagnostics immunoassay for detecting HCV core antigen. The multi-epitope fusion protein has two to six different non-overlapping linear peptides present in the amino acid sequence of hepatitis C virus (HCV) core protein, wherein each of the peptides is separated from the other peptides by a spacer consisting of a non-HCV amino acid sequence and having a chaperone amino acid sequence. No further HCV specific amino acid sequences are present in the polypeptide. A further aspect relates to a reagent kit for detecting HCV core antigen containing said multi-epitope fusion protein as calibrator or control or both.

13 Claims, 1 Drawing Sheet
Specification includes a Sequence Listing.

MULTI-EPITOPE FUSION PROTEIN OF AN HCV ANTIGEN AND USES THEREOF

CROSS-REFERENCE TO RELATED APPLICATIONS

This application is a continuation of International Application No. PCT/EP2018/069985 filed Jul. 24, 2018, which claims priority to European Application No. 17183523.4 filed Jul. 27, 2017, the disclosures of which are hereby incorporated by reference in their entirety.

BACKGROUND OF THE INVENTION

Reliable controls and calibrator material are essential parts of serological in vitro diagnostics assays, in particular in the infectious diseases area. For supporting the diagnosis of viral infections nucleic acid testing and detection of viral antigens belong to the methods well known in the art. Hepatitis C is a worldwide spread viral infection caused by the hepatitis C virus (HCV), an RNA virus that affects the liver and tends to become chronic. HCV is transmitted by blood-to-blood contact (e.g. by intravenous drug use, blood transfusion, mother-to-child transmission during pregnancy/birth). Besides RNA testing the serological detection of HCV structural antigens such as the core antigen are common methods for an early phase detection of a hepatitis C infection.

Several commercial kits for detecting HCV core antigen are available in the market, such as Abbott Architect HCV Ag, Ortho HCV Core Ag EIA, Fujirebio Lumipulse II HCV core assay, Murex HCV Ag/Ab Combination, Bio-Rad Monolisa HCV Ag-Ab Ultra. Each of these assays needs calibration material to generate a reliable cut-off for the differentiation of negative and positive specimen. For quantitative assays calibration material may also be used to adjust the test system readout in order to show and prove a correlation between the instrument's measurement of the analyte being tested and the actual concentration of this analyte. In addition, also calibration verification or (quality) control material is needed. For quantitative assays such control material has a known concentration of the analyte and is tested in the same way as patient samples. The measurement of controls guarantees that the test system is accurately measuring samples throughout the reportable measuring range. For qualitative assays determining the mere presence of the analyte the measurement of controls ensures that the test system is working properly and therefore can be counted on to produce quality results.

For HCV core in vitro diagnostic assays either native sera from infected patients or recombinantly produced HCV core antigen is used as calibration material and often also as control material. In view of the effective therapeutic treatment of HCV infections the availability of HCV positive patient sera becomes increasingly challenging. Therefor it is an option to produce recombinant HCV core antigen and then spike native sera or artificial matrices and buffer systems with the recombinant material. However, it has to be carefully assessed that the recovery in such artificially produced matrices is very close to the recovery in native sera and that the artificial matrix itself does not cause any interferences.

Only little is known about the stability of HCV core antigen in human sera or plasma. Tanaka et al. (Hepatol Res 2003, 26(4):261-267) describe that HCV core antigen is quite stable against heat stress when incubated at 25° C. for 7 days. After this stress procedure an ELISA is still able to detect HCV core antigen. However, we found out that the reactivity of core-antigen positive human sera as well as the reactivity of samples spiked with recombinant HCV core antigen decreases considerably when stored at room temperature for several days.

An object of the invention is therefore to provide material with higher long-term stability and longer shelf life for calibrating and controlling HCV immunoassays that overcome the observed limitations.

SUMMARY OF THE INVENTION

The invention relates to a multi-epitope fusion protein as well as to its use as calibrator and/or control in an in vitro diagnostics immunoassay for detecting HCV core antigen. The multi-epitope fusion protein comprises two to six different non-overlapping linear peptides present in the amino acid sequence of hepatitis C virus (HCV) core protein, wherein each of said different peptides is present one to five-fold in said multi-epitope fusion protein and each of said different peptides is separated from the other said peptides by a spacer consisting of a non-HCV amino acid sequence comprising a chaperone amino acid sequence. No further HCV specific amino acid sequences are present in said polypeptide.

In an embodiment, each of said linear peptides has a length of 5 to 50 amino acids and in another embodiment three different linear peptides are present in the multi-epitope fusion protein. A further aspect relates to a reagent kit for detecting HCV core antigen comprising a multi-epitope fusion antigen comprising said multi-epitope fusion protein as calibrator or control or both.

LEGEND TO THE DISCLOSED AMINO ACID SEQUENCES

SEQ ID NO:1, HCV core, genotype 1a (isolate 1) according to UniProt No. P26664, 191 amino acids

```
MSTNPKPQKK NKRNINRRPQ DVKFPGGGQI VGGVYLLPRR

GPRLGVRATR KTSERSQPRG RRQPIPKARR PEGRTWAQPG

YPWPLYGNEG CGWAGWLLSP RGSRPSWGPT DPRRRSRNLG

KVIDTLTCGF ADLMGYIPLV GAPLGGAARA LAHGVRVLED

GVNYATGNLP GCSFSIFLLA LLSCLTVPAS A
```

SEQ ID NO:2, HCV envelope E1, genotype 1a (isolate 1) according to UniProt No. P26664, 192 amino acids

```
YQVRNSTGLY HVTNDCPNSS IVYEAADAIL HTPGCVPCVR

EGNASRCWVA MTPTVATRDG KLPATQLRRH IDLLVGSATL

CSALYVGDLC GSVFLVGQLF TFSPRRHWTT QGCNCSIYPG

HITCHRMAWD MMMNWSPTTA LVMAQMLRIP QAILDMIAGA

HWGVLAGIAY FSMVGNWAKV LVVLLLFAGV DA
```

SEQ ID NO:3, HCV envelope E2, genotype 1a (isolate 1) according to UniProt No. P26664, 363 amino acids

```
ETHVTGGSAG HTVSGFVSLL APGAKQNVQL INTNGSWHLN

STALNCNDSL NTGWLAGLFY HHKFNSSGCP ERLASCRPLT
```

```
DFDQGWGPIS YANGSGPDQR PYCWHYPPKP CGIVPAKSVC

GPVYCFTPSP VVVGTTDRSG APTYSWGEND TDVFVLNNTR

PPLGNWFGCT WMNSTCFTKV CGAPPCVIGG AGNNTLHCPT

DCFRKHPDAT YSRCGSGPWI TPRCLVDYPY RLWHYPCTIN

YTIFKIRMYV GCVEHRLEAA CNWTRGERCD LEDRDRSELS

PLLLTTTQWQ VLPCSFTTLP ALSTGLIHLH QNIVDVQYLY

GVGSSIASWA IKWEYVVLLF LLLADARVCS CLWMMLLISQ

AEA
```

SEQ ID NO:4, HCVcore-3-epitopes calibrator (HCVcore-3Epi-EcS-FP), 432 amino acids; three different HCV core epitopes separated by two *E. coli* SlyD spacer polypeptides. The underlined parts are three different HCV core peptides.

```
MRGSGRRQPI PKARRPEGRT GGGSGGGMKV AKDLVVSLAY

QVRTEDGVLV DESPVSAPLD YLHGHGSLIS GLETALEGHE

VGDKFDVAVG ANDAYGQYDE NLVQRVPKDV FMGVDELQVG

MRFLAETDQG PVPVEITAVE DDHVVVDGNH MLAGQNLKFN

VEVVAIREAT EEELAHGHVH GAHDHHHDHD HDGGGSGGGL

LSPRGSRPSW GPTDPRRRSR GGGSGGGMKV AKDLVVSLAY

QVRTEDGVLV DESPVSAPLD YLHGHGSLIS GLETALEGHE

VGDKFDVAVG ANDAYGQYDE NLVQRVPKDV FMGVDELQVG

MRFLAETDQG PVPVEITAVE DDHVVVDGNH MLAGQNLKFN

VEVVAIREAT EEELAHGHVH GAHDHHHDHD HDGGGSGGGA

HGVRVLEDGV NYATGNLPGG GGSGGGHHHH HH
```

SEQ ID NO:5, HCVcore-3-epitopes calibrator (HCVcore-3Epi-EcS-FP, XY(Z, extralong, C/A)), 473 amino acids; three different HCV core epitopes separated by two *E. coli* SlyD spacer polypeptides. The underlined parts are three different HCV core peptides.

```
MRGSGRRQPI PKARRPEGRT GGGSGGGMKV AKDLVVSLAY

QVRTEDGVLV DESPVSAPLD YLHGHGSLIS GLETALEGHE

VGDKFDVAVG ANDAYGQYDE NLVQRVPKDV FMGVDELQVG

MRFLAETDQG PVPVEITAVE DDHVVVDGNH MLAGQNLKFN

VEVVAIREAT EEELAHGHVH GAHDHHHDHD HDGGGSGGGL

LSPRGSRPSW GPTDPRRRSR GGGSGGGMKV AKDLVVSLAY

QVRTEDGVLV DESPVSAPLD YLHGHGSLIS GLETALEGHE

VGDKFDVAVG ANDAYGQYDE NLVQRVPKDV FMGVDELQVG

MRFLAETDQG PVPVEITAVE DDHVVVDGNH MLAGQNLKFN

VEVVAIREAT EEELAHGHVH GAHDHHHDHD HDGGGSGGGD

PRRRSRNLGK VIDTLTAGFA DLMGYIPLVG APLGGAARAL

AHGVRVLEDG VNYATGNLPG GGGSGGGHHH HHH
```

SEQ ID NO:6, HCVcore-3-epitopes calibrator (HCVcore-3Epi-EcS-FP, XY(Z)4), 513 amino acids; three different HCV core epitopes separated by two *E. coli* SlyD spacer polypeptides. The underlined parts represent three different HCV core peptides. The C-terminal epitope is present four times whereas the two other epitopes are present as single epitopes.

```
MRGSGRRQPI PKARRPEGRT GGGSGGGMKV AKDLVVSLAY

QVRTEDGVLV DESPVSAPLD YLHGHGSLIS GLETALEGHE

VGDKFDVAVG ANDAYGQYDE NLVQRVPKDV FMGVDELQVG

MRFLAETDQG PVPVEITAVE DDHVVVDGNH MLAGQNLKFN

VEVVAIREAT EEELAHGHVH GAHDHHHDHD HDGGGSGGGL

LSPRGSRPSW GPTDPRRRSR GGGSGGGMKV AKDLVVSLAY

QVRTEDGVLV DESPVSAPLD YLHGHGSLIS GLETALEGHE

VGDKFDVAVG ANDAYGQYDE NLVQRVPKDV FMGVDELQVG

MRFLAETDQG PVPVEITAVE DDHVVVDGNH MLAGQNLKFN

VEVVAIREAT EEELAHGHVH GAHDHHHDHD HDGGGSGGGA

HGVRVLEDGV NYATGNLPGG GGSGGGAHGV RVLEDGVNYA

TGNLPGGGGS GGGAHGVRVL EDGVNYATGN LPGGGGSGGG

AHGVRVLEDG VNYATGNLPG GGGSGGGHHH HHH
```

DETAILED DESCRIPTION OF THE INVENTION

Recombinant antigens that correspond to the naturally occurring antigen are deemed to effectively imitate the natural analyte. Partial sequences of HCV antigens have been widely described in prior art. WO2016/172121 describes hepatitis C virus core antigen polypeptides that comprise partial sequences of the full length core antigen. The disclosed antigens can be used as immunogens for producing camelid antibodies and for subsequent screening. This publication is silent with regard to stability problems, nor does it disclose any information on the use of a core antigen as calibrator or control. However, we observed that independently of the matrix used (serum, plasma or artificial matrices such as e.g. aqueous buffers) a hepatitis C core antigen with a size close to the native full-length core antigen loses its reactivity in each of these matrices to a considerable extent within several days. The reason for this instability is not known but could be due to proteolytic or chemical degradation or masking of the antigen by other substances contained in said matrix. Also mechanical and thermal stress may influence the stability of HCV core antigen.

Surprisingly, when only short sections of the core antigen were used as multi-epitope fusion antigen in an in vitro diagnostics immunoassay and applied instead of an almost full-length core antigen (168 amino acids) the resulting signal recovery was very high in a heat-stress test at 35° C. for 14 days. While the signal of recombinant multi-epitope fusion protein decreased less than 10% the full-length core antigen showed a continuous signal loss to about two-thirds of the original signal.

The invention therefore concerns a multi-epitope fusion protein comprising two to six different non-overlapping linear peptides present in the amino acid sequence of hepatitis C virus (HCV) core protein wherein each of said different peptides is present one to five-fold in said multi-epitope fusion protein and each of said different peptides is separated from the other said peptides by a spacer consisting of a non-HCV amino acid sequence comprising a chaperone amino acid sequence and wherein no further HCV specific amino acid sequences are present in said polypeptide.

The term "multi-epitope fusion protein" is synonymous with "multi-epitope fusion antigen". A multi-epitope fusion protein comprises more than one epitope which is a binding site that is specifically recognized and bound by antibodies, such as antibodies applied as reagents in an immunoassay for detecting said epitopes.

The multi-epitope fusion protein according to the present invention contains epitopes of only HCV core protein. This means that the two to six different non-overlapping linear peptides represent distinct epitopes of core protein but not of a mixture of e.g. core and envelope peptides. Hepatitis C multi-epitope fusion antigens as described in prior art such as in the international patent application WO97/44469 or by Chien et al. (J Clin Microbiol 1999, 37(5): 1393-1397), wherein several viral proteins or epitopes of several viral proteins are part of a multi-epitope fusion protein such as HCV core, env, NS3 and NS4, are not encompassed by the current invention. In contrast to prior art the multi-epitope fusion proteins of the current invention contain epitopes present in naturally occurring HCV core antigen. The amino acid sequence of a representative HCV core protein (genotype 1a, isolate 1) is shown in SEQ ID NO:1. SEQ ID NOs. 2 and 3 show the amino acid sequences of envelope 1 (E1) and envelope 2 (E2), respectively.

The multi-epitope fusion protein comprises two to six different non-overlapping linear peptides, in an embodiment of three different linear peptides, present in the amino acid sequence of hepatitis C virus (HCV) core protein as described above. Linear peptides are amino acids linked via a peptide linkage in direct sequence, one after the other, where the individual amino acids are adjacent and covalently linked to each other. The multi-epitope fusion protein is a continuous, non-interrupted and contiguous chain of covalently linked amino acids.

The term "non-overlapping" means that the selected amino acid regions are separate epitopes that do not have overlapping amino acid sequences in common within the natural core antigen. For illustration, when the core epitope of amino acid positions 60-75 is selected as an epitope an additionally selected epitope may start at position 76 or may end at position 59. A combination of epitopes at positions 60-75, 97-117 and 152-171 is an example that fulfills the requirement of non-overlap.

An epitope within this multi-epitope fusion protein usually comprises at least 5 amino acids on a contiguous polypeptide chain, in an embodiment between 5 to 50 amino acids, in an embodiment 5 to 31 amino acids, in an embodiment 5 to 25 amino acids, in an embodiment 7 to 21 amino acids, in an embodiment 15 to 21 amino acids.

The term peptide and polypeptide are understood as synonyms in this specification, referring to molecules of up to 50 amino acids. The term protein refers to polypeptides of more than 50 amino acids. An antigen can be either a polypeptide or a protein. The term antigen refers to the fact that antibodies can specifically bind to it. An antigen comprises at least one epitope (binding site for antibodies) but usually harbors more than one epitope.

Usually, the peptides contained in the multi-epitope fusion protein are selected in such a way that the linear peptide sequences correspond to the epitopes recognized by those antibodies that are applied as specific reagents in an immunoassay that detects an HCV structural protein, in an embodiment HCV core antigen. The individual peptides mimic certain epitopes of the native analyte. It is important that the artificially composed multi-epitope fusion protein reacts in a very similar manner with the specifiers of the assay, i.e. the analyte-specific binding agents, as it is the case with core protein in natural samples. Otherwise an in vitro diagnostics assay cannot be appropriately calibrated. In an embodiment, three different non-overlapping linear peptides are part of the multi-epitope fusion protein. In another embodiment, said three different linear peptides comprise a linear amino acid sequence present within amino acid positions 55 to 80 of SEQ ID NO:1, amino acid positions 90 to 120 of SEQ ID NO:1 and amino acid positions 145 to 175 of SEQ ID NO:1. In a further embodiment said three different linear peptides consist of amino acid positions 60 to 75 of SEQ ID NO:1, amino acid positions 97 to 117 of SEQ ID NO:1 and amino acid positions 152 to 171 of SEQ ID NO:1. In another embodiment said three different linear peptides consist of amino acid positions 60 to 75 of SEQ ID NO:1, amino acid positions 97 to 117 of SEQ ID NO:1 and amino acid positions 111 to 171 of SEQ ID NO:1.

Also variants of SEQ ID NO:1 are encompassed, such as the core antigens of different HCV genotypes. These variants may easily be created by a person skilled in the art by conservative or homologous substitutions of the disclosed amino acid sequences (such as e.g. substitutions of a cysteine by alanine or serine). The term "variants" in this context also relates to a polypeptide substantially similar to said polypeptide. In particular, a variant may be an isoform which shows amino acid exchanges, deletions or insertions compared to the amino acid sequence of the most prevalent protein isoform. In one embodiment, such a substantially similar protein has an amino acid sequence identity to the most prevalent isoform of the protein of at least 90%, in another embodiment at least 95%. A variant of SEQ ID NO:1 is e.g. the core amino acid sequence of HCV genotypes 1 to 7. HCV genotypes, their prevalence and global distribution have been well-described in the art and summarized e.g. by Messina et al., Hepatology 2015 61(1), p. 77-87.

Apart from the two to six different non-overlapping linear peptides no further HCV-specific amino acid sequences are present in said multi-epitope fusion protein. The terms "no further HCV-specific amino acid sequences" and "non-HCV amino acid sequence" mean that further amino acid stretches can be part of the multi-epitope fusion protein. However, if non-HCV specific amino acid sequences are present an antibody raised against any of these non-HCV-specific sequences would not bind to an HCV structural antigen such as core antigen with a high affinity. The affinity of such an antibody to an HCV structural antigen would be less than $10^3$ l/mol. Only the two to six different peptides are able to immunoreact with antibodies in a patient sample or with the antibodies that are used as specific immunoassay reagents for detecting an HCV structural protein. Typically, an antibody that specifically binds to an HCV structural protein in an immunoassay has an affinity to said protein of at least $10^7$ l/mol, in an embodiment of at least $10^9$ l/mol.

In an embodiment, the two to six linear peptides are selected in such a way that the chosen sequences do not overlap.

In yet another embodiment, the invention concerns a multi-epitope fusion protein having the formula X-spacer-Y-spacer-Z, wherein X, Y and Z designate different non-overlapping linear amino acid sequences present in HCV core protein; wherein spacer designates a sequence of non-HCV amino acids and comprises a chaperone amino acid sequence. In an embodiment each of X, Y and Z is present one to five-fold. In another embodiment Z is present one to five-fold. All explanations and definitions provided further above apply also to this embodiment. In an embodiment, X comprises a linear amino acid sequence present within amino acid positions 55 to 80 of SEQ ID NO:1, Y comprises a linear amino acid sequence present within amino acid positions 90 to 120 of SEQ ID NO:1 and Z comprises a linear amino acid sequences present within amino acid positions 145 to 175 of SEQ ID NO:1. In an embodiment, X consists of amino acid positions 60 to 75 of SEQ ID NO:1, Y consists of amino acid positions 97 to 117 of SEQ ID NO:1 and Z consists of amino acid positions 152 to 171 of SEQ ID NO:1, in an embodiment Z consists of amino acid positions 111 to 171 of SEQ ID NO:1.

The two to six different non-overlapping linear peptides are separated by a spacer that consists of an amino acid sequence that is not present in the hepatitis C polyprotein, in particular that is not present in any of the HCV structural antigens core or env. Any non-HCV polypeptide with a length of at least 25 non-HCV amino acids, in an embodiment at least 100, in an embodiment at least 150, in an embodiment at least 200, in an embodiment 25 to 200 non-HCV amino acids may serve as a spacer. In an embodiment, the spacer comprises an amino acid sequence of a chaperone or any other protein that does not immunologically cross-react with the antibodies that are supposed to bind to the HCV-specific peptides. In an embodiment, said chaperone is selected from the group consisting of SlyD, SlpA, FkpA and Skp.

Each of the different peptides may be present one to five-fold in the multi-epitope fusion protein. This means that there are identical repetitions of an individual epitope. These repetitive epitopes do not need to be separated by a chaperone amino acid sequence but may be separated by a spacer that contains non-chaperone sequences such as short non-HCV peptides. As an example a spacer comprising 2 to 15 amino acids like repeated glycine residues may separate the identical HCV core epitopes. A further example of a spacer separating the identical epitopes is the amino acid sequence GGGSGGG.

In a further aspect, the multi-epitope fusion protein can be flanked by further non-HCV amino acids that might e.g. be present due to cloning procedures or may be required for purification purposes. These additional amino acids can be attached to the N-terminal or the C-terminal end or to both ends.

In another embodiment, the multi-epitope fusion protein consists of SEQ ID NO:4. In a further embodiment it consists of SEQ ID NO: 5 or 6.

An additional aspect of the invention concerns a method of producing a soluble multi-epitope fusion protein as described in the sections above, comprising the steps of a) culturing host cells transformed with an expression vector comprising operably linked a recombinant DNA molecule encoding a multi-epitope fusion protein as detailed above, b) expression of said polypeptide and c) purification of said polypeptide. Recombinant DNA technology is known to a person skilled in the art and has been extensively described in prior art e.g. by Sambrook et al., (1989, Molecular Cloning: A Laboratory Manual). Yet another aspect of the invention is an expression vector comprising operably linked a recombinant DNA molecule according to the present invention, i.e., a recombinant DNA molecule encoding a multi-epitope fusion protein comprising two to six different linear peptides present in the amino acid sequence of one hepatitis C virus (HCV) structural protein wherein each of said peptides is separated from the other said peptides by a spacer consisting of a non-HCV amino acid sequence and wherein no further HCV-specific amino acid sequences are present in said polypeptide.

An additional aspect is a method for producing a soluble, stable and immunoreactive multi-epitope fusion protein comprising two to six different non-overlapping linear peptides of HCV core antigen. This method comprises the steps of a) culturing host cells transformed with the above-described expression vector containing a gene encoding said multi-epitope fusion protein b) expression of the gene encoding said multi-epitope fusion protein c) purification of said multi-epitope fusion protein In another embodiment the invention concerns the use of a multi-epitope fusion protein comprising amino acid sequences of an HCV core protein as disclosed in this specification as calibrator and/or control material in an in vitro diagnostics test for detecting HCV core antigen.

The calibration of an in vitro diagnostics (IVD) instrument running an immunoassay for detecting HCV antigen works as follows: A calibration procedure of an IVD instrument for a specific assay is usually done according to the appropriate operator manual for analyzer-specific assay instructions. Generally every reagent pack is calibrated using the provided calibrator material. As an example: For HCV core antigen, different core-specific antibodies are used in a labeled format and/or in a format that enables the antibodies to be attached on a solid phase. The calibrator material, in an embodiment a multi-epitope fusion protein as described herein, is incubated with the specific core antibodies and processed in the same way as a sample. After detection of a signal this result is compared with the pre-defined values and the appropriate measuring range is set. Depending on the manufacturer's instructions calibration is repeated at pre-defined intervals or as required, e.g. if quality control findings are outside the specified limits.

In an embodiment the multi-epitope fusion protein as defined herein is used as material for quality control. This means that the multi-epitope fusion protein is used in a pre-defined concentration instead of a sample in order to verify that the IVD system is working properly and—in particular for quantitative assays—is measuring accurately.

Yet a further aspect of the invention is a method for detecting HCV core antigen. Said method applies a multi-epitope fusion protein as described in detail further above as calibrator or control material or both. In an embodiment, said method comprises the steps a) forming an immunoreaction admixture by admixing a body fluid sample with at least one HCV core antigen-specific binding agent; b) maintaining said immunoreaction admixture for a time period sufficient for allowing HCV core antigen present in the body fluid sample to immunoreact with said at least one HCV core antigen-specific binding agent to form an immunoreaction product; and c) detecting the presence and/or the concentration of any of said immunoreaction product, wherein a multi-epitope fusion protein as disclosed in this specification is used as a calibrator and/or control material.

Immunoassays for detection of proteins are well known in the art, and so are methods for carrying out such assays and practical applications and procedures. In an embodiment, the multi-epitope fusion protein is used in the sandwich format, wherein said multi-epitope fusion protein is bound by at least two antibodies, a labeled antibody and an antibody that enables attachment to a solid phase. However, as the multi-epitope fusion protein serves as calibrator and/or control material it mimics the analyte so that any principle of detection (e.g., enzyme immunoassay, electrochemiluminescence assay, radioisotope assay etc.) or the assay format (e.g., test strip assay, sandwich assay, indirect test concept or homogenous assay, etc.) can be chosen.

In an embodiment of the invention the immunoassay is a particle-based immunoassay applying microparticles as solid phase. A "particle" as used herein means a small, localized object to which can be ascribed a physical property such as volume, mass or average size. Microparticles may accordingly be of a symmetrical, globular, essentially globular or spherical shape, or be of an irregular, asymmetric shape or form. The size of a particle envisaged by the present invention may vary. In one embodiment the microparticles used are of globular shape, e.g. microparticles with a diameter in the nanometer and micrometer range. In one embodiment the microparticles used in a method according to the present disclosure have a diameter of 50 nanometers to 20 micrometers. In a further embodiment the microparticles have a diameter of between 100 nm and 10 µm. In one embodiment the microparticles used in a method according to the present disclosure have a diameter of 200 nm to 5 µm or from 750 nm to 5 µm.

Microparticles as defined herein above may comprise or consist of any suitable material known to the person skilled in the art, e.g. they may comprise or consist of or essentially consist of inorganic or organic material. Typically, they may comprise or consist of or essentially consist of metal or an alloy of metals, or an organic material, or comprise or consist of or essentially consist of carbohydrate elements. Examples of envisaged material for microparticles include agarose, polystyrene, latex, polyvinyl alcohol, silica and ferromagnetic metals, alloys or composition materials. In one embodiment the microparticles are magnetic or ferromagnetic metals, alloys or compositions. In further embodiments, the material may have specific properties and e.g. be hydrophobic, or hydrophilic. Such microparticles typically are dispersed in aqueous solutions and retain a small negative surface charge keeping the microparticles separated and avoiding non-specific clustering.

In one embodiment of the present invention, the microparticles are paramagnetic microparticles and the separation of such particles in the measurement method according to the present disclosure is facilitated by magnetic forces. Magnetic forces are applied to pull the paramagnetic or magnetic particles out of the solution/suspension and to retain them as desired while liquid of the solution/suspension can be removed and the particles can e.g. be washed and resuspended.

All biological liquids known to the expert can be used as isolated samples. The samples usually used are bodily liquids like whole blood, blood serum, blood plasma, urine, cerebrospinal fluid (liquor) or saliva, in an embodiment blood serum or plasma.

Another part of the invention concerns a reagent kit for the detection of HCV core antigen, comprising in separate containers or in separated compartments of a single container at least one HCV core antigen-specific binding agent and at least one multi-epitope fusion protein as defined in this specification as calibrator material.

The term single container relates to the fact that for many automatic analyzers, like the Elecsys® analyzer series from Roche diagnostics, the reagents required to measure a certain analyte are provided in the form of a reagent pack, i.e. as one container unit fitting on the analyzer and containing in different compartments all the key reagents required for measurement of the analyte of interest.

In an embodiment, the kit comprises at least two HCV core antigen-specific binding agents, wherein one of said at least two HCV core antigen-specific binding agents is detectably labeled. In addition, microparticles as defined above may be part of the reagent kit. In an embodiment, the reagent kit contains microparticles that are coated with a first partner of a binding pair and the second of the said at least two HCV core antigen-specific binding agents is bound to a second partner of said binding pair.

In another aspect, the kit comprises an additional separate container comprising a multi-epitope fusion protein as described herein as control material.

In addition, the reagent kits defined above contain controls and standard solutions as well as reagents in one or more solutions with the common additives, buffers, salts, detergents and the like as used by the average man skilled in the art along with instructions for use.

The following embodiments are also part of the invention:

1. A multi-epitope fusion protein comprising two to six different non-overlapping linear peptides present in the amino acid sequence of hepatitis C virus (HCV) core protein wherein each of said different peptides is present one to five-fold and each of said different peptides is separated from the other said peptides by a spacer consisting of a non-HCV amino acid sequence comprising a chaperone amino acid sequence and wherein no further HCV-specific amino acid sequences are present in said polypeptide.

2. A multi-epitope fusion protein according to any of embodiment 1, wherein said HCV core protein corresponds to an amino acid sequence shown in SEQ ID NO: 1.

3. A multi-epitope fusion protein according to any of embodiments 1 to 2, wherein each of said two to six linear peptides has a length of 5 to 50 amino acids, in an embodiment 5 to 31 amino acids, in an embodiment 5 to 25 amino acids, in an embodiment 7 to 21 amino acids, in an embodiment 15 to 21 amino acids.

4. A multi-epitope fusion protein according to any of embodiments 1 to 3, wherein three different linear peptides present in the amino acid sequence of one hepatitis C virus (HCV) structural protein are part of said multi-epitope fusion protein.

5. A multi-epitope fusion protein according to any of embodiments 1 to 4, wherein said three different linear peptides comprise a linear amino acid sequence present within amino acid positions 55 to 80 of SEQ ID NO:1, amino acid positions 90 to 120 of SEQ ID NO:1 and amino acid positions 145 to 175 of SEQ ID NO:1.

6. A multi-epitope fusion protein according to any of embodiments 1 to 5, wherein said three different linear peptides consist of amino acid positions 60 to 75 of SEQ ID NO:1, amino acid positions 97 to 117 of SEQ ID NO:1 and amino acid positions 152 to 171 of SEQ ID NO:1.

7. A multi-epitope fusion protein according to any of embodiments 1 to 6, having the formula X-spacer-Y-spacer-Z wherein X, Y and Z designate different non-overlapping linear amino acid sequences present in HCV core protein; wherein spacer designates a sequence of non-HCV amino acids comprising a chaperone amino acid sequence.

8. A multi-epitope fusion protein according to embodiment 7, wherein X comprises a linear amino acid sequence present within amino acid positions 55 to 80 of SEQ ID NO:1, Y comprises a linear amino acid sequence present within amino acid positions 90 to 120 of SEQ ID NO:1, Z comprises a linear amino acid sequences present within amino acid positions 145 to 175 of SEQ ID NO:1.

9. A multi-epitope fusion protein according to any of embodiments 7 to 8, wherein X consists of amino acid positions 60 to 75 of SEQ ID NO:1, Y consists of amino acid positions 97 to 117 of SEQ ID NO:1 and Z consists of amino acid positions 152 to 171 of SEQ ID NO:1.

10. A multi-epitope fusion protein according to any of embodiments 1 to 9, wherein said spacer comprises a sequence of at least 25 non-HCV amino acids, in an embodiment at least 100, in an embodiment at least 150, in an embodiment at least 200, in an embodiment 25 to 200 non-HCV amino acids.

11. A multi-epitope fusion protein according to any of embodiments 1 to 10, wherein said chaperone is selected from the group consisting of SlyD, SlpA, FkpA and Skp.

12. A multi-epitope fusion protein according to any of embodiments 1 to 11, consisting of an amino acid sequence selected from the group consisting of SEQ ID NOs:4, 5 and 6

13. A method of producing a soluble multi-epitope fusion protein, said method comprising the steps of
  a) culturing host cells transformed with an expression vector comprising operably linked a recombinant DNA molecule encoding a multi-epitope fusion protein according to any of embodiments 1 to 12,
  b) expression of said polypeptide and
  c) purification of said polypeptide.

14. Use of a multi-epitope fusion protein comprising amino acid sequences of an HCV core protein according to any of embodiments 1 to 12 as calibrator and/or control material in an in vitro diagnostics test for detecting an HCV antigen, in an embodiment HCV core antigen.

15. A method for detecting HCV core antigen in an immunoassay wherein a multi-epitope fusion protein according to any of embodiments 1 to 12 is used as calibrator and/or control material.

16. A method for detecting HCV core antigen in an isolated sample said method comprising a) forming an immunoreaction admixture by admixing a body fluid sample with at least one HCV core antigen-specific binding agent
  b) maintaining said immunoreaction admixture for a time period sufficient for allowing HCV core antigen present in the body fluid sample to immunoreact with said at least one HCV core antigen-specific binding agent to form an immunoreaction product; and
  c) detecting the presence and/or the concentration of any of said immunoreaction product, wherein a multi-epitope fusion protein according to any of embodiments 1 to 12 is used as a calibrator and/or control material.

17. A reagent kit for the detection of HCV core antigen, comprising in separate containers or in separated compartments of a single container at least one HCV core antigen-specific binding agent and at least one multi-epitope fusion protein according to any of embodiments 1 to 12 as calibrator material.

18. A reagent kit according to embodiment 17, comprising at least two HCV core antigen-specific binding agents, wherein one of said at least two HCV core antigen-specific binding agents is detectably labeled.

19. A reagent kit according to any of embodiments 17 and 18, additionally comprising microparticles.

20. A reagent kit according to embodiment 19, wherein said microparticles are coated with a first partner of a binding pair and the second of the said at least two HCV core antigen-specific binding agents is bound to a second partner of said binding pair.

21. A reagent kit for the detection of HCV core antigen according to embodiment 17, comprising an additional separate container comprising a multi-epitope fusion protein according to any of embodiments 1 to 12 as control material.

Figure 1:
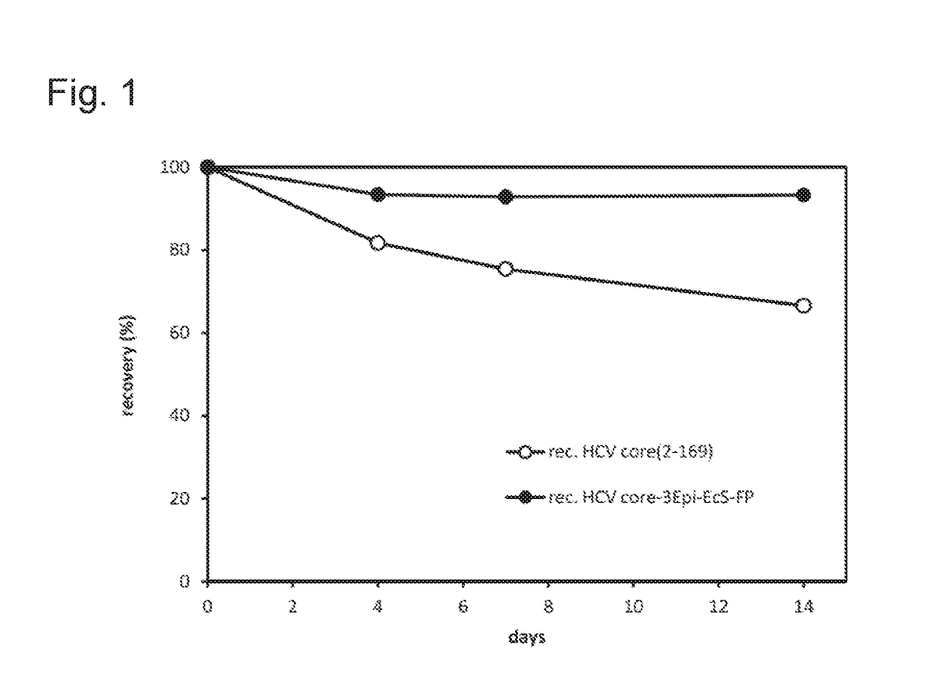
FIG. 1: shows the signal recovery of both recombinant HCV core antigens (almost full-length recombinant HCV core rec. HCV core (2-169) and rec. HCV core-3Epi-EcS-FP) after 35° C. stress over 14 days.

As described above, FIG. 1 shows the signal recovery of both recombinant HCV core antigens (almost full-length recombinant HCV core rec. HCV core (2-169) and rec. HCV core-3Epi-EcS-FP) after 35° C. stress over 14 days. At day 0 (no heat stress yet), in order to compare both calibrators, the signals of both calibrators are set as 100%. However, during the heat stress period (35° C. incubation of the calibrator) the calibrator comprising a multi-epitope fusion protein is superior to the core (2-169) calibrator: The signal of rec. HCV core-3Epi-EcS-FP decreased less than 10% after 4 days and remained stable throughout the following days of heat stress. The continuous signal loss of HCV core (2-169) to about two-thirds of the original signal was much more significant over the period of time observed. This situation reflects realistic conditions when reagent kits containing calibrators and/or controls are stored under inappropriate conditions such as during transportation under hot weather conditions. Also the shelf life of the calibrator that may be part of a kit is increased. For stability reasons multi-epitope fusion proteins such as the rec. HCV core-3Epi-EcS-FP are much more suitable as calibrator or/and control reagent than the full length or close to full length recombinant calibrator HCV core (2-169).

Table 1 shows results of an immunoassay described in example 4 where a multi-epitope fusion protein according to the invention was applied as "Cal2" (positive calibrator containing 350 pg/ml rec. HCV core-3Epi-EcS-FP as analyte analog). "Cal1" is the negative calibrator (pooled normal samples) that does not contain any HCV antigen. The signal provided with the Cal2 calibrator is about 12-fold higher than the signal obtained for a normal (negative) sample pool, providing an excellent measuring range so that the assay is able to discriminate between positive and negative results. "COI" means cut-off index and is a ratio obtained by dividing the measured signal by the pre-determined cut-off. The cut-off is the threshold for discriminating negative from positive samples. In this case, the cut-off is determined by multiplying the mean value of the positive calibrator Cal2 with 0.2 (see table 1), resulting in 2041 counts as cut-off. Samples with counts below this number are classified as negative and samples with more than 2041 counts are classified as positive (reactive or infected) samples.

Turning to the measuring results, the value obtained for a normal (negative) sample is very close to the negative (Cal 1) calibrator. The same is true for blood donor samples which are all detected as negative. On the other hand, also positive (HCV-infected) samples are correctly detected as positive. In other words, the multi-epitope fusion protein as described in this specification serves as reliable material for calibrating immunoassays for detecting HCV structural antigens and in particular for detecting HCV core antigen.

Figure 2:
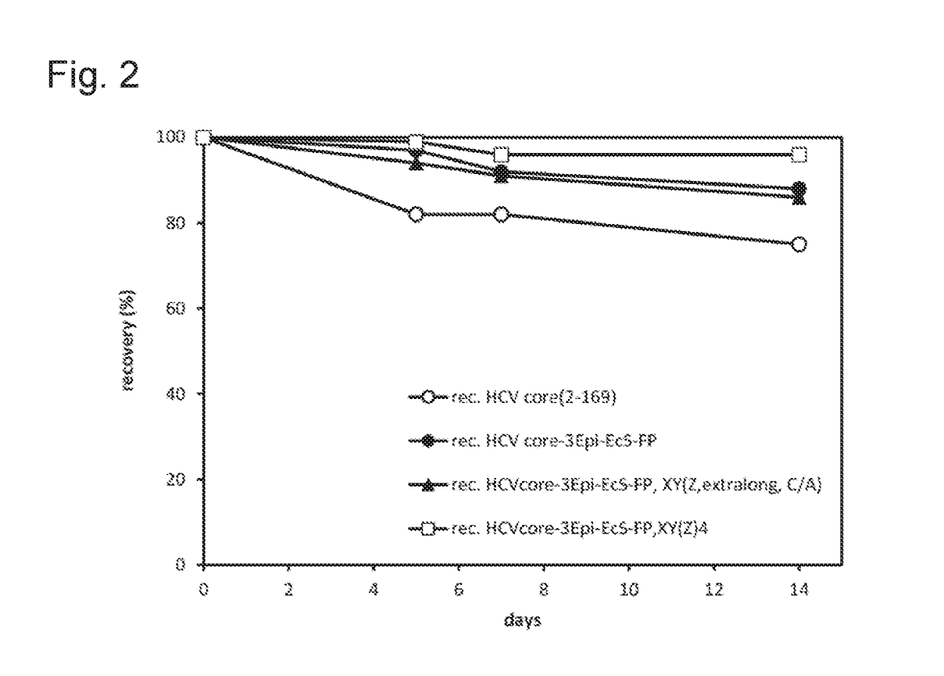
FIG. 2: depicts the results of an independent experiment carried out as described for FIG. 1 expanded by the additional multi-epitope fusion proteins rec. HCVcore-3Epi-EcS-FP, XY(Z,extralong, C/A) and rec. HCVcore-3Epi-EcS-FP,XY(Z)4.

As described above, FIG. 2 depicts the results of an independent experiment carried out as described for FIG. 1 expanded by the additional multi-epitope fusion proteins rec. HCVcore-3Epi-EcS-FP, XY(Z,extralong, C/A) and rec. HCVcore-3Epi-EcS-FP,XY(Z)4. Consistently, for stability reasons multi-epitope fusion proteins such as the rec. HCV core-3Epi-EcS-FP, rec. HCVcore-3Epi-EcS-FP, XY(Z,extralong, C/A) and rec. HCVcore-3Epi-EcS-FP,XY(Z)4 are much more suitable as calibrator or/and control reagent than the full length or close to full length recombinant calibrator HCV core(2-169).

Table 2 reports results of an independent experiment carried out as described for Table 1 and described in example 4 where additional multi-epitope fusion proteins according to the invention were applied as "Cal2" (positive calibrator containing 400 pg/ml rec. HCVcore-3Epi-EcS-FP, XY(Z,extralong, C/A) or 520 pg/ml rec. HCVcore-3Epi-EcS-FP,XY(Z)4 as analyte analog). Beside rec. HCVcore-3Epi-EcS-FP the multi-epitope fusion proteins rec. HCVcore-3Epi-EcS-FP, XY(Z,extralong, C/A) and rec. HCVcore-3Epi-EcS-FP,XY(Z)4 also serve as reliable material for calibrating immunoassays for detecting HCV structural antigens and in particular for detecting HCV core antigen.

TABLE 1

Data for normal, blood donor and HCV positive samples, calibration with multi-epitope fusion protein

| | sample ID | counts | COI |
|---|---|---|---|
| Cal1 | pooled normal samples | 836 | 0.41 |
| | | 854 | 0.42 |
| Cal2 | rec. HCV core-3Epi-EcS-FP | 10'248 | 5.02 |
| | | 10'160 | 4.98 |
| CutOff: 0.2 * mean Cal2 | | 2'041 | |
| normal sample | #Dia62058 | 735 | 0.36 |
| HCV antigen | #9224787 | 97'627 | 47.84 |
| positive samples | #9233117 | 9'324 | 4.57 |
| | #217293 | 68'481 | 33.56 |
| | #9220121 | 359'798 | 176.30 |
| | #9220337 | 4'139 | 2.03 |
| blood donors | BRK_2401 | 808 | 0.40 |
| | BRK_2402 | 722 | 0.35 |
| | BRK_2403 | 781 | 0.38 |
| | BRK_2404 | 785 | 0.38 |
| | BRK_2405 | 798 | 0.39 |
| | BRK_2406 | 773 | 0.38 |
| | BRK_2407 | 825 | 0.40 |
| | BRK_2408 | 816 | 0.40 |
| | BRK_2409 | 755 | 0.37 |
| | BRK_2410 | 738 | 0.36 |
| | BRK_2413 | 796 | 0.39 |
| | BRK_2414 | 800 | 0.39 |
| | BRK_2415 | 800 | 0.39 |
| | BRK_2416 | 841 | 0.41 |
| | BRK_2418 | 799 | 0.39 |
| | BRK_2419 | 793 | 0.39 |
| | BRK_2420 | 707 | 0.35 |
| | BRK_2421 | 753 | 0.37 |
| | BRK_2422 | 789 | 0.39 |
| | BRK_2423 | 814 | 0.40 |
| | BRK_2424 | 786 | 0.39 |

TABLE 2

Data for normal, blood donor and HCV positive samples, calibration with further multi-epitope fusion proteins

| | sample ID | Counts rec. HCVcore-3Epi-EcS-FP, XY(Z,extra-long, C/A) | COI | Counts rec. HCVcore-3Epi-EcS-FP,XY(Z)4 | COI |
|---|---|---|---|---|---|
| Cal1 | pooled normal samples | 926 | 0.45 | | 0.44 |
| | | 923 | 0.44 | | 0.44 |
| Cal2 | | 10'323 | 4.96 | | |
| | | 10'484 | 5.04 | | |
| | | | | 10'389 | 4.99 |
| | | | | 10'440 | 5.01 |
| CutOff: 0.2 * mean Cal2 | | 2'081 | | 2'083 | |
| normal sample | #59067614 | 882 | 0.42 | | 0.42 |
| HCV antigen | #9224787 | 98'037 | 47.11 | | 47.07 |
| positive samples | #9233117 | 7'782 | 3.74 | | 3.74 |
| | #217293 | 72'900 | 35.03 | | 35.00 |
| | #9220121 | 319'605 | 153.58 | | 153.43 |
| | #9220337 | 4'098 | 1.97 | | 1.97 |
| blood donors | BRK_2401 | 868 | 0.42 | | 0.42 |
| | BRK_2402 | 902 | 0.43 | | 0.43 |
| | BRK_2403 | 895 | 0.43 | | 0.43 |
| | BRK_2404 | 887 | 0.43 | | 0.43 |
| | BRK_2405 | 915 | 0.44 | | 0.44 |
| | BRK_2406 | 876 | 0.42 | | 0.42 |
| | BRK_2407 | 873 | 0.42 | | 0.42 |
| | BRK_2408 | 902 | 0.43 | | 0.43 |
| | BRK_2409 | 888 | 0.43 | | 0.43 |
| | BRK_2410 | 880 | 0.42 | | 0.42 |
| | BRK_2413 | 852 | 0.41 | | 0.41 |
| | BRK_2414 | 894 | 0.43 | | 0.43 |
| | BRK_2415 | 909 | 0.44 | | 0.44 |
| | BRK_2416 | 884 | 0.42 | | 0.42 |
| | BRK_2418 | 901 | 0.43 | | 0.43 |

TABLE 2-continued

Data for normal, blood donor and HCV positive samples, calibration with further multi-epitope fusion proteins

| sample ID | Counts rec. HCVcore-3Epi-EcS-FP, XY(Z,extra-long, C/A) | COI | Counts rec. HCVcore-3Epi-EcS-FP,XY(Z)4 | COI |
|---|---|---|---|---|
| BRK_2419 | 898 | 0.43 | | 0.43 |
| BRK_2420 | 903 | 0.43 | | 0.43 |
| BRK_2421 | 917 | 0.44 | | 0.44 |
| BRK_2422 | 893 | 0.43 | | 0.43 |
| BRK_2423 | 880 | 0.42 | | 0.42 |
| BRK_2424 | 890 | 0.43 | | 0.43 |

The invention is further illustrated by the Examples.

EXAMPLES

Example 1: Methods

Monoclonal Antibodies

Recombinant HCV core antigen needed for immunization of appropriate animals was obtained using standard techniques known in the art by inserting a DNA fragment encoding the desired antigen amino acid sequence into an *E. coli* expression plasmid followed by overexpression and purification of the protein. These standard molecular biological methods are described for example in Sambrook, J. et al., Molecular cloning: A laboratory manual; Cold Spring Harbor Laboratory Press, Cold Spring Harbor, N.Y., 1989.

Murine or rabbit monoclonal antibodies against HCV core were prepared by standard hybridoma technology or by recombinant nucleic acid techniques as known to the skilled person and in an analogous manner as described e.g. in WO2016/091755, respectively.

Monoclonal antibodies against HCV core protein used as capture compounds in the examples below bind to the epitopes aa 157-169 and aa 65-71 of the HCV core protein (SEQ ID NO:1). Very similar epitopes and their determination have already been disclosed in EP1308507. As detection compound, a monoclonal antibody was chosen capable of binding to the core epitope aa 102-112, an epitope related to epitopes also described in EP0967484 and EP1308507. For the immunization of mice and rabbits, HCV core antigenic sequences of genotype 1a according to Genbank Acc. No: P26664.3 GI:130455 (SEQ ID NO:1), which discloses the complete polyprotein encoded by HCV genotype 1 were used.

In particular, peptides either from amino acid 110-171 as recombinant fusion protein with Escherichia coli SlyD following the procedure disclosed in WO 03/000878 A2, US 2009/0291892 A1, WO 2013/107633 A1 or peptides from amino acid 2-169 as recombinant protein following the procedure described by Boulant, S. et al., 2005, J. Virol. 79:11353-11365 were used for immunization. In an additional approach peptides from amino acid 82-117 coupled to KLH (keyhole limpet hemocyanin) were used for immunization according to known methods.

Recombinant HCV Core Antigens Used as Calibrator/Control Reagent

The recombinant HCV core antigen from amino acid 2-169 (rec. HCV core(2-169)) was prepared following the procedure described by Boulant, S. et al., 2005, J. Virol. 79:11353-11365.

The synthetic genes encoding the recombinant HCV core antigen fusion protein containing the epitopes of the three monoclonal anti-HCV core antibodies described above and two *E. coli* SlyD units (rec. HCV core-3Epi-EcS-FP, SEQ ID NO. 4) was purchased from Eurofins MWG Operon (Ebersberg, Germany). On the basis of the pET24a expression plasmid of Novagen (Madison, Wis., USA) the following cloning steps were performed. The vector was digested with NdeI and XhoI and a cassette comprising the described fusion protein was inserted. The insert of the resulting plasmid was sequenced and found to encode the desired fusion protein. The amino acid sequences of the resulting protein (SEQ ID NO. 4) is shown in the sequence protocol of the present invention. It contained a C-terminal hexahistidine tag to facilitate Ni-NTA-assisted purification. The rec. HCV core-3Epi-EcS-FP was purified according to the following protocol. *E. coli* BL21 (DE3) cells harboring the expression plasmid were grown in LB medium plus kanamycin (30 µg/ml) to an $OD_{600}$ of 1, and cytosolic overexpression was induced by adding isopropyl-β-D-thiogalactosid (IPTG) to a final concentration of 1 mM at a growth temperature of 37° C. 4 hours after induction, cells were harvested by centrifugation (20 min at 5000×g), frozen and stored at −20° C. For cell lysis, the frozen pellet was resuspended in 20 mM Tris buffer pH 8.0, 10 mM $MgC_{12}$, 10 U/ml Benzonase®, 1 tablet Complete® and 1 tablet Complete® EDTA-free per 50 ml of buffer (protease inhibitor cocktail) and the resulting suspension was lysed by high pressure homogenization. The crude lysate was supplemented up to 20 mM imidazole. After centrifugation the supernatant was applied onto a Ni-NTA (nickel-nitrilotriacetate) column pre-equilibrated in buffer A (100 mM sodium phosphate pH 8.0, 300 mM sodium chloride, 20 mM imidazole, 1 tablet Complete® EDTA-free per 50 ml of buffer). Prior to elution, the imidazole concentration was raised to 40 mM in order to remove contaminant proteins. The proteins were then eluted by applying an imidazole concentration of 250 mM. After dialysis the protein was further purified by ion-exchange chromatography (Q-Sepharose). Finally, the protein was subjected to size exclusion chromatography and the protein-containing fractions were pooled.

Protein Determination

The protein concentration of purified polypeptides was determined by determining the optical density (OD) at 280 nm, using the molar extinction coefficient calculated on the basis of the amino acid sequence of the polypeptide or using the colorimetric BCA method.

Example 2: Synthesis of Activated Biotinylation Reagents

Biotin-PEGn-NHS-biotinylation reagents (CAS-Nr. 365441-71-0; n=number of ethylene oxide units) were either obtained from IRIS Biotech GmbH or synthesized in house.

In the de novo synthesis the control of discrete number of ethylene oxide units was ensured by the stepwise elongation of shorter PEGs, such as tetraethylene glycol, following the described method from Chen and Baker, J. Org. Chem. 1999, 64, 6840-6873.

In a first step bis-trityl-$PEG_n$ 1 has been obtained (as obvious, n represents the number of ethylene glycol units).

Deprotection of 1 was carried out by stirring in 1M HCl in dioxane for 1 h at room temperature. After evaporation the residue was refluxed in methanol until a clear solution was obtained and the flask was kept at 4° C. overnight. After filtration the solution was extracted with hexane, the methanolic layer evaporated and dried to give the corresponding $PEG_n$-diol 2 as oil or wax (consistency depending on length/number of units (n) of the PEG).

Next the introduction of the acid function was carried out by sodium catalyzed addition of $PEG_n$-diol to tert-butyl acrylate according to Seitz and Kunz, J. Org. Chem. 1997, 62, 813-826. This way compound 3 is obtained.

To a solution of HO-$PEG_n$-COOtBu 3 (1 equivalent) and triethylamine (2.5 equivalents) in methylene chloride methylsulfonyl chloride (2 equivalents) was added drop-wise at 0° C. After stirring for 1 h aqueous work-up and evaporation followed.

The mesylate 4 (1 equivalent) was directly reacted with $NaN_3$ (2 equivalents) by stirring in dimethylformamide at room temperature for two days. After removal of the solids and dimethylformamide, aqueous work-up with diethylether and $Na_2CO_3$ followed.

The crude product 5 was purified by column chromatography on silica gel in ethyl acetate/methanol 15/1. Reduction of the azide 5 (1 equivalent) was performed by stirring for 24 h with triphenylphosphine (1.1 equivalents) in tetrahydrofurane/water 4/1 at room temperature. After evaporation the residue was suspended in water and washed with ethyl acetate several times. The water layer was evaporated and dried to give the amine 6 as colorless oil.

Cleavage of the tert-butyl ester was carried out with 5% trifluoroacetic acid in water. Amino-$PEG_n$-acid 7 was obtained by evaporation with water for several times.

Biotin was introduced by coupling with corresponding N-hydroxysuccinimide ester 8 (1.05 equivalents) with triethylamine (4 equivalents) in dimethylformamide at room temperature overnight. After evaporation crude product 9 was purified by RP-HPLC in acetonitrile/water.

Finally, N-hydroxysuccinimide ester 10 was formed by reaction with N-hydroxysuccinimide (1.1 equivalents) and ethyl dimethylaminopropyl carbodiimide (1.1 equivalents) in methylene chloride. After completion of the reaction, the reaction mixture was diluted with methylene chloride and washed with water. Evaporation and drying led to pure Biotin-$PEG_n$-NHS 10 as oil, wax or solid, respectively depending on the number of ethylene oxide units.

Scheme 1 Synthesis of Biotin-PEG(n)-NHS

Example 3: Labeling of Antibodies

Coupling of biotin and ruthenium moieties, respectively, to antibodies:

Antibodies were obtained and purified according to state-of-the-art procedures that are fully familiar to a person skilled in the art.

Prior to labeling, the detection antibody was cleaved by pepsin to obtain a F(ab')$_2$ fragment and to eliminate the interference prone Fc fragment (the method is described by A. Johnstone and R. Thorpe in Immunochemistry in Practice, Blackwell Scientific 1987). The purified F(ab')$_2$ fragment was further polymerized with the homobifunctional crosslinker disuccinimidyl suberate (DSS) and applied to a S400 gel filtration chromatography to gather the optimal size range of the F(ab')$_2$ polymer (the principle is described in DE3640412).

For the attachment of the respective label, in general the lysine ε-amino groups of the antibodies were targeted by N-hydroxy-succinimide activated compounds. At a protein concentration of 10 mg/ml, antibodies were reacted with N-hydroxy-succinimide activated biotinylation reagents (Biotin-PEG24-NHS) and N-hydroxy-succinimide activated ruthenium labeling reagents, respectively. The label/protein ratio of biotinylation or ruthenium labeling reagent was 5-6:1 or 15:1, respectively. The reaction buffer was 50 mM potassium phosphate (pH 8.5), 150 mM KCl. The reaction was carried out at room temperature for 15 minutes and stopped by adding L-lysine to a final concentration of 10 mM. To avoid hydrolytic inactivation of the labels, the respective stock solutions were prepared in dried DMSO (Sigma-Aldrich, Germany). After the coupling reaction, unreacted free biotin or ruthenium label was removed by passing the crude antibody conjugate through a gel filtration column (Superdex 200 HI Load) or by dialysis.

Example 4: Prototype Elecsys HCV Core Antigen Assay

Measurements of an Elecsys HCV core antigen prototype assay were carried out in a sandwich assay format on an automated cobas® e601 or e801 analyzers (Roche Diagnostics GmbH). Signal detection in this analyzer is based on electrochemiluminescence. In this sandwich assay the one or more capture antibody-biotin-conjugates (i.e. analyte-specific binding agents) is/are immobilized on the surface of a streptavidin-coated magnetic bead. The detection-antibody (further analyte-specific binding agent) bears a complexed ruthenium cation as the signaling moiety. In the presence of analyte, the ruthenium complex is bridged to the solid phase and emits light at 620 nm after excitation at the platinum electrode comprised in the measuring cell of the analyzer. The signal output is in arbitrary light units. Measurements were performed with HCV core antigen positive and negative human serum and plasma samples purchased from several sources (Tables 1 and 2) as well as the recombinant antigens HCV core(2-169, corresponding to amino acid positions 2 to 169 of SEQ ID NO:1) and HCV core-3Epi-EcS-FP (SEQ ID NO:4, Table 1 and FIGS. 1 & 2), HCVcore-3Epi-EcS-FP, XY(Z, extralong, C/A) (SEQ ID NO:5, Table 2 and FIG. 2) and HCVcore-3Epi-EcS-FP, XY(Z)4 (SEQ ID NO:6, Table 2 and FIG. 2).

The experimental HCV core antigen assay was conducted as follows. 50 µl of normal human serum, HCV antigen positive sample or recombinant antigens HCV core(2-169) or HCV core-3Epi-EcS-FP or HCVcore-3Epi-EcS-FP, XY(Z, extralong, C/A) or HCVcore-3Epi-EcS-FP, XY(Z)4 in a 36 mM HEPES-Buffer containing 5.4% mannitol and 5.9% D(+)-sucrose, 0.01% N-methylisothiazolone-hydrochloride, 0.1% oxypyrion and 0.4% bovine albumin and 25 µl of a detergent containing pretreatment reagent (PT: 0.25 M KOH, 1.125 M KCl, 1.5% hexadecyltrimethylammoniumchloride (HTAC), 0.85% octylglycoside) were incubated together for 9 minutes to release the antigen followed by the addition of 35 µl of a mixture of two different antibody-biotin conjugates (1.5 µg/ml and 0.9 µg/mL) and 40 µl of 1.2 µg/ml detection antibody ruthenium label conjugate in the same assay buffer R1 and R2 (200 mM Tris, pH 7.0, 225 mM KCl, 0.5% sodium taurodeoxycholate, 0.3% zwittergent 3-14, 0.1% oxypyrion, 0.01% methylisothiazolinone, 0.2% bovine serum albumin, 0.2% bovine IgG, 50 µg/ml MAK33-IgG1, 50 µg/ml MAK33-F(ab')$_2$-Poly, 50 µg/ml MAK IgG2b/Fab2a-Poly). After additional 9 minutes incubation time 50 µl streptavidin-coated paramagnetic microparticles were added and incubated for further 9 minutes. Afterwards, the HCV core antigen was detected (via the electrochemiluminescent signal generated in these experiments).

---

The invention claimed is:

1. A multi-epitope fusion protein comprising: two to six different non-overlapping linear peptides of hepatitis C virus (HCV) core protein, wherein each of said two to six different non-overlapping linear peptides is at least 5 amino acids in length and present one to five-fold, and wherein each of said two to six different non-overlapping linear peptides is separated from the other said peptides by a spacer, wherein the spacer comprises a chaperone peptide specific of a chaperone protein, and wherein no further HCV specific amino acid sequences are present in said multi-epitope fusion protein.

2. A multi-epitope fusion protein according to claim 1, wherein said HCV core protein corresponds to an amino acid sequence of SEQ ID NO: 1.

3. A multi-epitope fusion protein according to claim 1, wherein each of said two to six linear peptides has a length of 5 to 50 amino acids.

4. A multi-epitope fusion protein according to claim 1, wherein three different linear peptides present in the amino acid sequence of said HCV core protein are part of said multi-epitope fusion protein.

5. A multi-epitope fusion protein according to claim 1, wherein said three different linear peptides comprises a linear amino acid sequence present within amino acid positions 55 to 80 of SEQ ID NO:1, amino acid positions 90 to 120 of SEQ ID NO:1 and amino acid positions 145 to 175 of SEQ ID NO:1.

6. A multi-epitope fusion protein according to claim 1, having the formula

X-spacer-Y-spacer-Z wherein X, Y and Z designate different non-overlapping linear peptides of HCV core protein;
wherein Z is present one to five-fold and
wherein spacer designates a chaperone peptide.

7. A multi-epitope fusion protein according to claim 6, wherein X comprises a linear amino acid sequence present within amino acid positions 55 to 80 of SEQ ID NO:1, Y comprises linear amino acid sequence present within amino acid positions 90 to 120 of SEQ ID NO:1, Z comprises linear amino acid sequences present within amino acid positions 145 to 175 of SEQ ID NO:1.

8. A multi-epitope fusion protein according to claim 1, wherein said spacer comprises a sequence of at least 25 non-HCV amino acids.

9. A multi-epitope fusion protein according to claim 1, consisting of any of SEQ ID NOs:4 to 6.

10. A method of producing a soluble multi-epitope fusion protein, said method comprising the steps of
    a) culturing host cells transformed with an expression vector comprising operably linked a recombinant DNA molecule encoding a multi-epitope fusion protein according to claim 1,
    b) expression of said polypeptide and
    c) purification of said polypeptide.

11. A reagent kit for the detection of HCV core antigen, comprising in separate containers or in separated compartments of a single container at least one HCV core antigen-specific binding agent and at least one multi-epitope fusion protein according to claim 1 as calibrator material.

12. A reagent kit according to claim 11, comprising at least two HCV core antigen-specific binding agents, wherein one of said at least two HCV core antigen-specific binding agents is detectably labeled.

13. A reagent kit according to claim 11, additionally comprising microparticles.

* * * * *

SEQUENCE LISTING

<160> NUMBER OF SEQ ID NOS: 6

<210> SEQ ID NO 1
<211> LENGTH: 191
<212> TYPE: PRT
<213> ORGANISM: Hepatitis C virus

<400> SEQUENCE: 1

```
Met Ser Thr Asn Pro Lys Pro Gln Lys Lys Asn Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
            180                 185                 190
```

<210> SEQ ID NO 2
<211> LENGTH: 192
<212> TYPE: PRT
<213> ORGANISM: Hepatitis C virus

<400> SEQUENCE: 2

```
Tyr Gln Val Arg Asn Ser Thr Gly Leu Tyr His Val Thr Asn Asp Cys
1               5                   10                  15

Pro Asn Ser Ser Ile Val Tyr Glu Ala Ala Asp Ala Ile Leu His Thr
            20                  25                  30

Pro Gly Cys Val Pro Cys Val Arg Glu Gly Asn Ala Ser Arg Cys Trp
```

```
                35                  40                  45
Val Ala Met Thr Pro Thr Val Ala Thr Arg Asp Gly Lys Leu Pro Ala
            50                  55                  60

Thr Gln Leu Arg Arg His Ile Asp Leu Leu Val Gly Ser Ala Thr Leu
65                  70                  75                  80

Cys Ser Ala Leu Tyr Val Gly Asp Leu Cys Gly Ser Val Phe Leu Val
                85                  90                  95

Gly Gln Leu Phe Thr Phe Ser Pro Arg Arg His Trp Thr Thr Gln Gly
            100                 105                 110

Cys Asn Cys Ser Ile Tyr Pro Gly His Ile Thr Gly His Arg Met Ala
            115                 120                 125

Trp Asp Met Met Met Asn Trp Ser Pro Thr Thr Ala Leu Val Met Ala
            130                 135                 140

Gln Leu Leu Arg Ile Pro Gln Ala Ile Leu Asp Met Ile Ala Gly Ala
145                 150                 155                 160

His Trp Gly Val Leu Ala Gly Ile Ala Tyr Phe Ser Met Val Gly Asn
                165                 170                 175

Trp Ala Lys Val Leu Val Val Leu Leu Leu Phe Ala Gly Val Asp Ala
            180                 185                 190

<210> SEQ ID NO 3
<211> LENGTH: 363
<212> TYPE: PRT
<213> ORGANISM: Hepatitis C virus

<400> SEQUENCE: 3

Glu Thr His Val Thr Gly Gly Ser Ala Gly His Thr Val Ser Gly Phe
1               5                   10                  15

Val Ser Leu Leu Ala Pro Gly Ala Lys Gln Asn Val Gln Leu Ile Asn
            20                  25                  30

Thr Asn Gly Ser Trp His Leu Asn Ser Thr Ala Leu Asn Cys Asn Asp
                35                  40                  45

Ser Leu Asn Thr Gly Trp Leu Ala Gly Leu Phe Tyr His His Lys Phe
            50                  55                  60

Asn Ser Ser Gly Cys Pro Glu Arg Leu Ala Ser Cys Arg Pro Leu Thr
65                  70                  75                  80

Asp Phe Asp Gln Gly Trp Gly Pro Ile Ser Tyr Ala Asn Gly Ser Gly
                85                  90                  95

Pro Asp Gln Arg Pro Tyr Cys Trp His Tyr Pro Pro Lys Pro Cys Gly
            100                 105                 110

Ile Val Pro Ala Lys Ser Val Cys Gly Pro Val Tyr Cys Phe Thr Pro
            115                 120                 125

Ser Pro Val Val Val Gly Thr Thr Asp Arg Ser Gly Ala Pro Thr Tyr
            130                 135                 140

Ser Trp Gly Glu Asn Asp Thr Asp Val Phe Val Leu Asn Asn Thr Arg
145                 150                 155                 160

Pro Pro Leu Gly Asn Trp Phe Gly Cys Thr Trp Met Asn Ser Thr Gly
                165                 170                 175

Phe Thr Lys Val Cys Gly Ala Pro Pro Cys Val Ile Gly Gly Ala Gly
            180                 185                 190

Asn Asn Thr Leu His Cys Pro Thr Asp Cys Phe Arg Lys His Pro Asp
            195                 200                 205

Ala Thr Tyr Ser Arg Cys Gly Ser Gly Pro Trp Ile Thr Pro Arg Cys
            210                 215                 220
```

```
Leu Val Asp Tyr Pro Tyr Arg Leu Trp His Tyr Pro Cys Thr Ile Asn
225                 230                 235                 240

Tyr Thr Ile Phe Lys Ile Arg Met Tyr Val Gly Gly Val Glu His Arg
            245                 250                 255

Leu Glu Ala Ala Cys Asn Trp Thr Arg Gly Glu Arg Cys Asp Leu Glu
            260                 265                 270

Asp Arg Asp Arg Ser Glu Leu Ser Pro Leu Leu Leu Thr Thr Thr Gln
            275                 280                 285

Trp Gln Val Leu Pro Cys Ser Phe Thr Thr Leu Pro Ala Leu Ser Thr
            290                 295                 300

Gly Leu Ile His Leu His Gln Asn Ile Val Asp Val Gln Tyr Leu Tyr
305                 310                 315                 320

Gly Val Gly Ser Ser Ile Ala Ser Trp Ala Ile Lys Trp Glu Tyr Val
                325                 330                 335

Val Leu Leu Phe Leu Leu Leu Ala Asp Ala Arg Val Cys Ser Cys Leu
                340                 345                 350

Trp Met Met Leu Leu Ile Ser Gln Ala Glu Ala
                355                 360

<210> SEQ ID NO 4
<211> LENGTH: 432
<212> TYPE: PRT
<213> ORGANISM: Artificial
<220> FEATURE:
<223> OTHER INFORMATION: HCV core 3-epitopes calibrator

<400> SEQUENCE: 4

Met Arg Gly Ser Gly Arg Arg Gln Pro Ile Pro Lys Ala Arg Arg Pro
1               5                   10                  15

Glu Gly Arg Thr Gly Gly Gly Ser Gly Gly Gly Met Lys Val Ala Lys
            20                  25                  30

Asp Leu Val Val Ser Leu Ala Tyr Gln Val Arg Thr Glu Asp Gly Val
        35                  40                  45

Leu Val Asp Glu Ser Pro Val Ser Ala Pro Leu Asp Tyr Leu His Gly
    50                  55                  60

His Gly Ser Leu Ile Ser Gly Leu Glu Thr Ala Leu Glu Gly His Glu
65                  70                  75                  80

Val Gly Asp Lys Phe Asp Val Ala Val Gly Ala Asn Asp Ala Tyr Gly
                85                  90                  95

Gln Tyr Asp Glu Asn Leu Val Gln Arg Val Pro Lys Asp Val Phe Met
            100                 105                 110

Gly Val Asp Glu Leu Gln Val Gly Met Arg Phe Leu Ala Glu Thr Asp
        115                 120                 125

Gln Gly Pro Val Pro Val Glu Ile Thr Ala Val Glu Asp Asp His Val
    130                 135                 140

Val Val Asp Gly Asn His Met Leu Ala Gly Gln Asn Leu Lys Phe Asn
145                 150                 155                 160

Val Glu Val Val Ala Ile Arg Glu Ala Thr Glu Glu Glu Leu Ala His
                165                 170                 175

Gly His Val His Gly Ala His Asp His His His Asp His Asp His Asp
            180                 185                 190

Gly Gly Gly Ser Gly Gly Gly Leu Leu Ser Pro Arg Gly Ser Arg Pro
        195                 200                 205

Ser Trp Gly Pro Thr Asp Pro Arg Arg Arg Ser Arg Gly Gly Gly Ser
    210                 215                 220
```

```
Gly Gly Gly Met Lys Val Ala Lys Asp Leu Val Ser Leu Ala Tyr
225                 230                 235                 240

Gln Val Arg Thr Glu Asp Gly Val Leu Val Asp Glu Ser Pro Val Ser
            245                 250                 255

Ala Pro Leu Asp Tyr Leu His Gly His Gly Ser Leu Ile Ser Gly Leu
        260                 265                 270

Glu Thr Ala Leu Glu Gly His Glu Val Gly Asp Lys Phe Asp Val Ala
    275                 280                 285

Val Gly Ala Asn Asp Ala Tyr Gly Gln Tyr Asp Glu Asn Leu Val Gln
290                 295                 300

Arg Val Pro Lys Asp Val Phe Met Gly Val Asp Glu Leu Gln Val Gly
305                 310                 315                 320

Met Arg Phe Leu Ala Glu Thr Asp Gln Gly Pro Val Pro Val Glu Ile
            325                 330                 335

Thr Ala Val Glu Asp Asp His Val Val Val Asp Gly Asn His Met Leu
        340                 345                 350

Ala Gly Gln Asn Leu Lys Phe Asn Val Glu Val Val Ala Ile Arg Glu
    355                 360                 365

Ala Thr Glu Glu Glu Leu Ala His Gly His Val His Gly Ala His Asp
370                 375                 380

His His His Asp His Asp His Asp Gly Gly Ser Gly Gly Gly Ala
385                 390                 395                 400

His Gly Val Arg Val Leu Glu Asp Gly Val Asn Tyr Ala Thr Gly Asn
            405                 410                 415

Leu Pro Gly Gly Gly Ser Gly Gly His His His His His
            420                 425                 430

<210> SEQ ID NO 5
<211> LENGTH: 473
<212> TYPE: PRT
<213> ORGANISM: Artificial Sequence
<220> FEATURE:
<223> OTHER INFORMATION: HCVcore-3-epitopes calibrator
      (HCVcore-3Epi-EcS-FP, XY(Z, extralong, C/A))

<400> SEQUENCE: 5

Met Arg Gly Ser Gly Arg Arg Gln Pro Ile Pro Lys Ala Arg Arg Pro
1               5                   10                  15

Glu Gly Arg Thr Gly Gly Gly Ser Gly Gly Gly Met Lys Val Ala Lys
            20                  25                  30

Asp Leu Val Val Ser Leu Ala Tyr Gln Val Arg Thr Glu Asp Gly Val
        35                  40                  45

Leu Val Asp Glu Ser Pro Val Ser Ala Pro Leu Asp Tyr Leu His Gly
    50                  55                  60

His Gly Ser Leu Ile Ser Gly Leu Glu Thr Ala Leu Glu Gly His Glu
65                  70                  75                  80

Val Gly Asp Lys Phe Asp Val Ala Val Gly Ala Asn Asp Ala Tyr Gly
                85                  90                  95

Gln Tyr Asp Glu Asn Leu Val Gln Arg Val Pro Lys Asp Val Phe Met
            100                 105                 110

Gly Val Asp Glu Leu Gln Val Gly Met Arg Phe Leu Ala Glu Thr Asp
        115                 120                 125

Gln Gly Pro Val Pro Val Glu Ile Thr Ala Val Glu Asp Asp His Val
    130                 135                 140

Val Val Asp Gly Asn His Met Leu Ala Gly Gln Asn Leu Lys Phe Asn
145                 150                 155                 160
```

```
Val Glu Val Val Ala Ile Arg Glu Ala Thr Glu Glu Leu Ala His
                165                 170                 175

Gly His Val His Gly Ala His Asp His His Asp His Asp His Asp
            180                 185                 190

Gly Gly Gly Ser Gly Gly Gly Leu Leu Ser Pro Arg Gly Ser Arg Pro
                195                 200                 205

Ser Trp Gly Pro Thr Asp Pro Arg Arg Ser Arg Gly Gly Gly Ser
    210                 215                 220

Gly Gly Gly Met Lys Val Ala Lys Asp Leu Val Val Ser Leu Ala Tyr
225                 230                 235                 240

Gln Val Arg Thr Glu Asp Gly Val Leu Val Asp Glu Ser Pro Val Ser
                245                 250                 255

Ala Pro Leu Asp Tyr Leu His Gly His Gly Ser Leu Ile Ser Gly Leu
                260                 265                 270

Glu Thr Ala Leu Glu Gly His Glu Val Gly Asp Lys Phe Asp Val Ala
            275                 280                 285

Val Gly Ala Asn Asp Ala Tyr Gly Gln Tyr Asp Glu Asn Leu Val Gln
            290                 295                 300

Arg Val Pro Lys Asp Val Phe Met Gly Val Asp Glu Leu Gln Val Gly
305                 310                 315                 320

Met Arg Phe Leu Ala Glu Thr Asp Gln Gly Pro Val Pro Val Glu Ile
                325                 330                 335

Thr Ala Val Glu Asp Asp His Val Val Val Asp Gly Asn His Met Leu
                340                 345                 350

Ala Gly Gln Asn Leu Lys Phe Asn Val Glu Val Val Ala Ile Arg Glu
            355                 360                 365

Ala Thr Glu Glu Leu Ala His Gly His Val His Gly Ala His Asp
            370                 375                 380

His His His Asp His Asp His Asp Gly Gly Gly Ser Gly Gly Gly Asp
385                 390                 395                 400

Pro Arg Arg Arg Ser Arg Asn Leu Gly Lys Val Ile Asp Thr Leu Thr
                405                 410                 415

Ala Gly Phe Ala Asp Leu Met Gly Tyr Ile Pro Leu Val Gly Ala Pro
                420                 425                 430

Leu Gly Gly Ala Ala Arg Ala Leu Ala His Gly Val Arg Val Leu Glu
            435                 440                 445

Asp Gly Val Asn Tyr Ala Thr Gly Asn Leu Pro Gly Gly Gly Ser
    450                 455                 460

Gly Gly Gly His His His His His His
465                 470

<210> SEQ ID NO 6
<211> LENGTH: 513
<212> TYPE: PRT
<213> ORGANISM: Artificial Sequence
<220> FEATURE:
<223> OTHER INFORMATION: HCVcore-3-epitopes calibrator
      (HCVcore-3Epi-EcS-FP, XY(Z)4)

<400> SEQUENCE: 6

Met Arg Gly Ser Gly Arg Arg

```
                35                  40                  45
Leu Val Asp Glu Ser Pro Val Ser Ala Pro Leu Asp Tyr Leu His Gly
 50                  55                  60

His Gly Ser Leu Ile Ser Gly Leu Glu Thr Ala Leu Glu Gly His Glu
 65                  70                  75                  80

Val Gly Asp Lys Phe Asp Val Ala Val Ala Asn Asp Ala Tyr Gly
                 85                  90                  95

Gln Tyr Asp Glu Asn Leu Val Gln Arg Val Pro Lys Asp Val Phe Met
                100                 105                 110

Gly Val Asp Glu Leu Gln Val Gly Met Arg Phe Leu Ala Glu Thr Asp
                115                 120                 125

Gln Gly Pro Val Pro Val Glu Ile Thr Ala Val Glu Asp Asp His Val
                130                 135                 140

Val Val Asp Gly Asn His Met Leu Ala Gly Gln Asn Leu Lys Phe Asn
145                 150                 155                 160

Val Glu Val Val Ala Ile Arg Glu Ala Thr Glu Glu Leu Ala His
                    165                 170                 175

Gly His Val His Gly Ala His Asp His His Asp His Asp His Asp
                180                 185                 190

Gly Gly Gly Ser Gly Gly Gly Leu Leu Ser Pro Arg Gly Ser Arg Pro
                195                 200                 205

Ser Trp Gly Pro Thr Asp Pro Arg Arg Ser Arg Gly Gly Ser
210                 215                 220

Gly Gly Gly Met Lys Val Ala Lys Asp Leu Val Val Ser Leu Ala Tyr
225                 230                 235                 240

Gln Val Arg Thr Glu Asp Gly Val Leu Val Asp Ser Pro Val Ser
                    245                 250                 255

Ala Pro Leu Asp Tyr Leu His Gly His Gly Ser Leu Ile Ser Gly Leu
                260                 265                 270

Glu Thr Ala Leu Glu Gly His Glu Val Gly Asp Lys Phe Asp Val Ala
                275                 280                 285

Val Gly Ala Asn Asp Ala Tyr Gly Gln Tyr Asp Glu Asn Leu Val Gln
                290                 295                 300

Arg Val Pro Lys Asp Val Phe Met Gly Val Asp Glu Leu Gln Val Gly
305                 310                 315                 320

Met Arg Phe Leu Ala Glu Thr Asp Gln Gly Pro Val Pro Val Glu Ile
                325                 330                 335

Thr Ala Val Glu Asp Asp His Val Val Val Asp Gly Asn His Met Leu
                340                 345                 350

Ala Gly Gln Asn Leu Lys Phe Asn Val Glu Val Val Ala Ile Arg Glu
                355                 360                 365

Ala Thr Glu Glu Leu Ala His Gly His Val His Gly Ala His Asp
                370                 375                 380

His His His Asp His Asp His Asp Gly Gly Gly Ser Gly Gly Gly Ala
385                 390                 395                 400

His Gly Val Arg Val Leu Glu Asp Gly Val Asn Tyr Ala Thr Gly Asn
                    405                 410                 415

Leu Pro Gly Gly Gly Ser Gly Gly Gly Ala His Gly Val Arg Val
                420                 425                 430

Leu Glu Asp Gly Val Asn Tyr Ala Thr Gly Asn Leu Pro Gly Gly Gly
                435                 440                 445

Gly Ser Gly Gly Gly Ala His Gly Val Arg Val Leu Glu Asp Gly Val
450                 455                 460
```

```
Asn Tyr Ala Thr Gly Asn Leu Pro Gly Gly Gly Gly Ser Gly Gly Gly
465                 470                 475                 480

Ala His Gly Val Arg Val Leu Glu Asp Gly Val Asn Tyr Ala Thr Gly
                485                 490                 495

Asn Leu Pro Gly Gly Gly Gly Ser Gly Gly Gly His His His His His
            500                 505                 510

His
```